(12) United States Patent
Fiorini et al.

(10) Patent No.: US 11,266,990 B2
(45) Date of Patent: Mar. 8, 2022

(54) DEVICE AND METHOD FOR PERFORMING DIGITAL PCR

(71) Applicant: IMEC VZW, Leuven (BE)

(72) Inventors: Paolo Fiorini, Brussels (BE); Tim Stakenborg, Leuven (BE); Frederik Colle, Linden (BE)

(73) Assignee: IMEC VZW, Leuven (BE)

( * ) Notice: Subject to any disclaimer, the term of this patent is extended or adjusted under 35 U.S.C. 154(b) by 135 days.

(21) Appl. No.: 16/059,576

(22) Filed: Aug. 9, 2018

(65) Prior Publication Data

US 2018/0345287 A1 Dec. 6, 2018

Related U.S. Application Data

(62) Division of application No. 14/547,737, filed on Nov. 19, 2014, now abandoned.

(30) Foreign Application Priority Data

Nov. 29, 2013 (EP) .................................... 13195075

(51) Int. Cl.
*C12Q 1/686* (2018.01)
*B01L 3/00* (2006.01)
*B01L 7/00* (2006.01)

(52) U.S. Cl.
CPC .......... *B01L 3/502784* (2013.01); *B01L 7/52* (2013.01); *C12Q 1/686* (2013.01); *B01L 2200/061* (2013.01); *B01L 2200/0673* (2013.01); *B01L 2200/10* (2013.01); *B01L 2300/0627* (2013.01); *B01L 2300/0816* (2013.01); *B01L 2300/0867* (2013.01); *B01L 2300/0883* (2013.01); *B01L 2300/1827* (2013.01)

(58) Field of Classification Search
CPC ....... B01L 2200/061; B01L 2300/0627; B01L 3/502784; B01L 2200/0673; B01L 2200/10; B01L 7/52; B01L 2300/0867; B01L 2300/0883; B01L 2300/1827; C12Q 1/686; C12Q 1/68
See application file for complete search history.

(56) References Cited

U.S. PATENT DOCUMENTS

| | | | |
|---|---|---|---|
| 2003/0099018 A1 | 5/2003 | Singh et al. | |
| 2005/0202489 A1* | 9/2005 | Cho .................. | B01L 3/502715 435/6.12 |
| 2006/0008382 A1 | 1/2006 | Salamitou et al. | |
| 2009/0047713 A1 | 2/2009 | Handique | |
| 2011/0086352 A1 | 4/2011 | Bashir et al. | |
| 2012/0052560 A1* | 3/2012 | Knight .............. | B01L 3/502784 435/286.1 |
| 2012/0070818 A1* | 3/2012 | Rowlen .................. | G01N 15/14 435/3 |
| 2013/0084572 A1* | 4/2013 | Hindson .............. | C12Q 1/6851 435/6.12 |
| 2013/0210680 A1* | 8/2013 | Derda ................ | C12N 15/1037 506/26 |
| 2014/0248623 A1 | 9/2014 | Janaway et al. | |

FOREIGN PATENT DOCUMENTS

| | | |
|---|---|---|
| WO | 2008/005246 A2 | 1/2008 |
| WO | 2008/005248 A2 | 1/2008 |

OTHER PUBLICATIONS

Chen, P.C., "An evaluation of a real-time passive micromixer to the performance of a continuous flow type microfluidic reactor," BioChip J., published on-line September, vol. 7, No. 3, pp. 227-233. (Year: 2013).*
Zeng et al., "Programmable active droplet generation enabled integrated pneumatic micropumps," Lab Chip, vol. 13, pp. 267-273 (Year: 2012).*
Beer et al., "On-Chip, Real-Time, Single-Copy Polymerase Chain Reaction in Picoliter Droplets," Analytical Chemistry, vol. 79, pp. 8471-8475. (Year: 2007).*
Whale et al., "Comparison of microfluidic digital PCR and conventional quantitative PCR for measuring copy number variation," Nucleic Acids Research, vol. 40, No. 11, e82, pp. 1-9. (Year: 2012).*
European Search Report, European Patent Application No. 13195075. 0, dated Apr. 10, 2014, 5 pages.
Chen, Pin-Chuan, "An Evaluation of a Real-Time Passive Micromixer to the Performance of a Continuous Flow Type Microfluidic Reactor", BioChip, vol. 7, No. 3, Sep. 2013, pp. 227-233.

* cited by examiner

*Primary Examiner* — Young J Kim
(74) *Attorney, Agent, or Firm* — McDonnell Boehnen Hulbert & Berghoff LLP

(57) ABSTRACT

A micro-fluidic device 100 for performing digital PCR is presented. The device comprises: a semiconductor substrate; a first micro-fluidic channel 104, comprising an inlet 102 and an outlet 103, embedded in the semiconductor substrate; a heating element 101 thermally coupled to the first micro-fluidic channel 104; a droplet generator 107 connected to the inlet 102 of the first micro-fluidic channel 104 for generating droplets and pumping generated droplets at a flow rate into the first micro-fluidic channel 104; characterized in that: the heating element 101 is a single heating element connected to a temperature control unit 111 configured to cycle the temperature of the complete first micro-fluidic channel 104 through at least two temperature values; and wherein the flow rate of the droplet generator 107 is adaptable. Further, a method to perform digital PCR is presented using the micro-fluidic device 100.

6 Claims, 8 Drawing Sheets

DEVICE AND METHOD FOR PERFORMING DIGITAL PCR

CROSS-REFERENCE

This application is a divisional of U.S. patent application Ser. No. 14/547,737, filed Nov. 19, 2014, now abandoned, which claims priority from EP 13195075.0, filed Nov. 29, 2013, which is incorporated by reference in its entirety.

FIELD OF THE DISCLOSURE

The disclosure is related to micro-fluidic devices. In particular, the disclosure is related to methods and devices for performing digital Polymerase Chain Reaction (PCR) in lab-on-a-chip devices. More in particular, the disclosure is related to methods and devices for performing droplet based PCR.

BACKGROUND TO THE DISCLOSURE

State of the art describes two types of devices for performing PCR: static PCR systems and dynamic PCR systems. In static PCR systems, PCR is performed in a cavity in which a fluid is present. A disadvantage of these systems is the fixed volume of the cavity which cannot be increased by the user. Dynamic PCR systems allow continuous fluid processing. The devices use a fluidic channel and multiple heating elements (typically 3) for heating the fluidic channel. Underneath the fluidic channel, different heating elements with a fixed location are present. The temperature value for each heating element can be set by the user. A fluid sample propagates through the fluidic channel and is exposed to different temperatures of different heating elements. While propagating through the micro-fluidic channel, DNA present in the fluid sample in the fluidic channel is amplified. Typically, to prevent cross-heating between different heating zones, different heating elements are separated from each other by e.g. providing space between them. This reduces the compactness of the system. When the system is fabricated using a material with a large thermal conductivity like e.g. silicon, the distance between different heating zones even needs to be larger.

Another disadvantage of these systems is the number of heating cycles which is fixed by design as a fluidic channel traverses a fixed amount of times over a certain heating element. Another disadvantage is the duration of different temperature steps in a PCR cycle. The state of the art design allows users to modify the flow speed of a fluid sample, but the duration of all temperature steps is thereby changed. The user does not have the possibility to change the duration of a single temperature step. The ratio of the duration of different steps, which is an important parameter in PCR optimization, cannot be changed.

Accordingly, there is a need for micro-fluidic digital PCR devices which overcome at least some of the drawbacks described above.

SUMMARY OF THE DISCLOSURE

In a first aspect of the disclosure, a micro-fluidic device for performing digital PCR is presented. The device comprises: a semiconductor substrate; a first micro-fluidic channel, comprising an inlet and an outlet, embedded in the semiconductor substrate; a heating element thermally coupled to the first micro-fluidic channel; a droplet generator connected to the inlet of the first micro-fluidic channel for generating droplets and pumping generated droplets at a flow rate into the first micro-fluidic channel; wherein the heating element is a single heating element connected to a temperature control unit configured to cycle the temperature of the complete first micro-fluidic channel through at least two temperature values; and wherein the flow rate of the droplet generator is adaptable.

According to an embodiment of the disclosure, the micro-fluidic device further comprises a second micro-fluidic channel connected on one side to an outlet of the droplet generator and on the other side to the inlet of the first micro-fluidic channel; and a heating element located to heat generated droplets present in the second micro-fluidic channel.

According to an embodiment of the disclosure, the micro-fluidic device further comprises a detector located at the outlet of the first micro-fluidic channel for detecting droplets containing PCR products.

According to an embodiment of the disclosure, the micro-fluidic device further comprises a detector located for detecting droplets containing PCR products during PCR in the first micro-fluidic channel.

According to an embodiment of the disclosure, the micro-fluidic device further comprises a computing unit connected to the detector; and wherein the computing unit is configured for determining a percentage of droplets containing PCR products.

According to an embodiment of the disclosure, the droplet generator is connected to the computing unit and the droplet generator is reconfigurable for changing the number of copies of an analyte in droplets.

According to an embodiment of the disclosure, the micro-fluidic device further comprises at least one through-substrate trench at least partially surrounding the first micro-fluidic channel.

According to an embodiment of the disclosure, the micro-fluidic device further comprises a heating element located at the outlet at the outlet of the micro-fluidic channel for heating droplets.

In a second aspect of the disclosure, a method for performing a PCR on a fluid sample using a micro-fluidic device as described in the first aspect of the disclosure is presented. The method comprises: providing a fluid sample in the micro-fluidic device; generating droplets of the fluid sample and pumping the droplets into the first micro-fluidic channel using the droplet generator; and cycling the temperature of the complete first micro-fluidic channel through at least two temperature values using the single heating element.

According to an embodiment of the disclosure, generating droplets and pumping droplets is stopped when the first micro-fluidic channel is completely filled with droplets.

According to an embodiment of the disclosure, cycling the temperature of the first micro-fluidic channel is performed until a saturation level of an analyte in a droplet is reached.

According to an embodiment of the disclosure, cycling the temperature of the first micro-fluidic channel comprises continuously cycling the temperature of the first micro-fluidic channel through at least two temperature values while pumping droplets into the first micro-fluidic channel.

According to an embodiment of the disclosure, the droplets are pumped in the first micro-fluidic channel at a flow rate adapted to a duration of the temperature cycling of the first micro-fluidic channel.

According to an embodiment of the disclosure, the method further comprises: pre-heating the generated droplets before pumping the droplets into the first micro-fluidic channel.

According to an embodiment of the disclosure, the method further comprises: continuously heating droplets to increasing temperatures at the outlet of the first micro-fluidic channel.

According to an embodiment of the disclosure, the method further comprises detecting droplets containing PCR products using the detector.

According to an embodiment of the disclosure, the number of copies of an analyte in droplets is changed by the droplet generator depending on the percentage of droplets containing PCR products determined by the computing unit.

DETAILED DESCRIPTION OF THE DISCLOSURE

Figure 1:
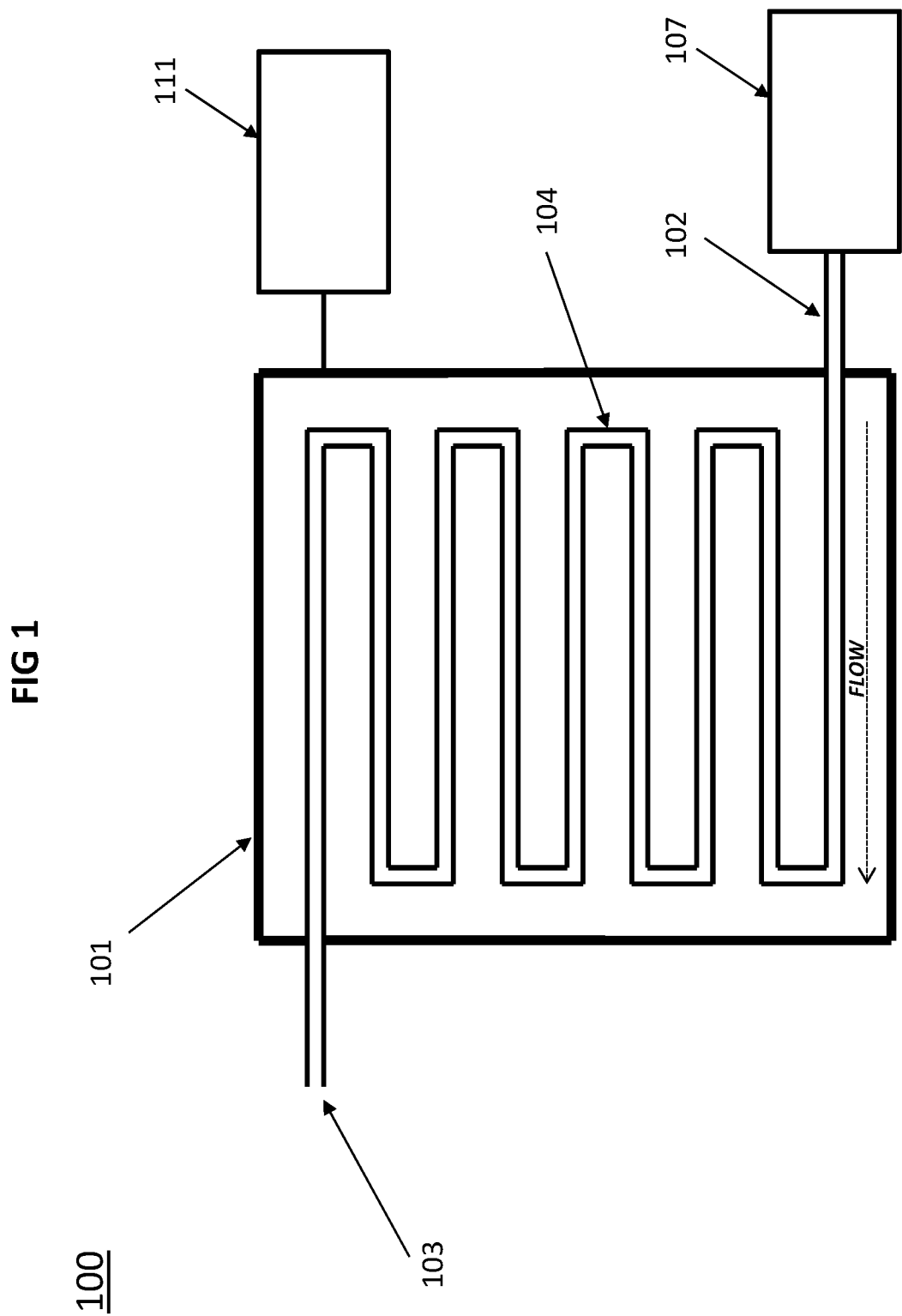
FIG. 1 illustrates an embodiment of the disclosure according to a first aspect of the disclosure

Where in embodiments of this disclosure reference is made to a "polymerase chain reaction (PCR)", this is a method for DNA amplification. It is a biochemical technology in molecular biology to amplify a single or a few copies of a piece of DNA across several orders of magnitude thereby generating copies of a particular DNA sequence.

Where in embodiments of this disclosure reference is made to a "lab-on-a-chip", this a device that integrates one or more laboratory functions on a single chip.

Where in embodiments of this disclosure reference is made to "micro-fluidic", this term refers to sizes of devices typically below 1 mm.

Where in embodiments of this disclosure reference is made to a semiconductor substrate, this may include a substrate such as e.g. a silicon (Si) substrate, a silica (SiO2) substrate, a silicon germanium (SiGe) substrate or a glass silicon substrate.

Where in embodiments of this disclosure reference is made to "droplets containing PCR products" this term refers to droplets in which amplification of an analyte has taken place through PCR. The term "PCR products" refers to the amplified analyte.

It is an object of the disclosure to obtain a PCR device which allows a user to have, during operation of the PCR device, full control over:
1) the duration of each temperature step of a PCR cycle;
2) the value of each temperature step value of different PCR cycles;
3) the flow speed of a fluid sample in the device; and
4) the volume to be processed through the device.

It is an object of the disclosure to obtain a single device which can be used for batch PCR and for continuous PCR without changing the design.

A polymerase chain reaction (PCR) is a technique for DNA amplification. It is a biochemical technology in molecular biology to amplify a single or a few copies of a piece of DNA across several orders of magnitude to generate copies of a particular DNA sequence. To perform PCR, a mixture containing reagents, DNA and primers is placed in a reactor. The temperature of the reactor is cycled through e.g. three temperature values. As a result, DNA in the reactor is amplified. The digital PCR reaction is a method for performing DNA assays by diluting target DNA in small droplets containing on average less than 1 DNA copy per droplet. Labels that fluoresce when bound to DNA are added to the reagent. Quantification of the amount of target DNA occurs by counting droplets that display fluorescent signals at the end of the PCR reaction. Due to the digital nature, digital PCR is especially suitable for performing high precision measurements of low target concentrations.

In a first aspect of the disclosure, a micro-fluidic device 100 for performing digital PCR is presented. The device comprises: a semiconductor substrate; a first micro-fluidic channel 104, comprising an inlet 102 and an outlet 103, embedded in the semiconductor substrate; a heating element 101 thermally coupled to the first micro-fluidic channel 104; a droplet generator 107 connected to the inlet 102 of the micro-fluidic channel 104 for generating droplets and pumping generated droplets at a flow rate into the first micro-fluidic channel 104; characterized in that: the heating element 101 is a single heating element connected to a temperature control unit 111 configured to cycle the temperature of the complete first micro-fluidic channel 104 through at least two temperature values; and wherein the flow rate of the droplet generator 107 is adaptable.

The device as presented in the first aspect of the disclosure may be used to perform continuous or static (batch) PCR. FIG. 1 illustrates such a device. The device 100 comprises a first micro-fluidic channel 104. The first micro-fluidic channel 104 comprises a single inlet 102 and a single outlet 103. The first micro-fluidic channel 104 interconnects the inlet 102 to the outlet 103. A droplet generator 107 for generating droplets from a fluid sample is connected to an inlet 102 of the microfluidic channel 104. The droplet generator 107 generates droplets and pumps the droplets in the first micro-fluidic channel 104. The flow rate of the droplet generator 107 is adaptable during operation. This flow rate of the droplet generator 107 is defined as the speed at which the droplet generator 107 pumps droplets into the first micro-fluidic channel 104. Thus, the propagation speed of droplets in the first micro-fluidic channel 104 is defined by the flow rate of the droplet generator 107. As an advantage, the flow rate of the droplets in the first micro-fluidic channel 104 and a temperature cycling of the first micro-fluidic channel 104 can be aligned. The flow rate of droplets in the first micro-fluidic channel 104 can be adjusted to the number of desired temperature cycles wherein each temperature cycle comprises at least two temperature values.

Example 1

When a certain PCR operation requires 30 temperature cycles of 30 seconds each, the flow rate of droplet generator 107 is adapted such that the duration of generated droplets propagating from inlet 102 to outlet 103 is equal to 900 seconds. In state of the art continuous flow PCR devices, the number of cycles is fixed by design, e.g. 30 cycles are fixed by design. When e.g. 32 cycles are needed, a re-design of the device is necessary.

Example 2

During a certain experiment, the necessary time for a complete PCR reaction may be 10 minutes. If the volume of the first micro-fluidic channel 104 is 2 uL, the total flow rate of droplets and carrier medium in the first micro-fluidic channel 104 should be 0.2 uL/min. The droplet generator 107 may be tuned to ensure that the total flow rate (of droplets and carrier medium) in the first micro-fluidic channel 104 is 0.2 uL/min. This flexibility is not present in state of the art devices.

The adaptability of the flow rate to the time required for performing a certain PCR makes the use of the presented micro-fluidic device very versatile.

The droplet generator 107 may comprise a carrier medium compartment. According to a specific embodiment of the disclosure, the carrier medium is oil and the carrier medium compartment is an oil compartment. The droplets may be generated in oil to separate the different droplets from each other. The droplet generator 107 comprises at least one inlet for providing a fluid sample and at least one outlet for exiting generated droplets of the fluid sample. According to a specific embodiment, the droplet generator 107 comprises at least two inlets; a first inlet for providing a fluid sample and a second inlet for providing oil. A single heating element 101 is present and located to change the temperature of the complete micro-fluidic channel 104. According to an embodiment of the disclosure, the heating element 101 may be located near the first micro-fluidic channel 104, e.g. underneath the first micro-fluidic channel 104, allowing a more uniform heat up of the complete first micro-fluidic channel 104. The heating element 101 is connected to a temperature control unit 111. The temperature control unit 111 is controls the heating element 101 and is configured to heat the first micro-fluidic channel 104 to at least two temperature values. The temperature control unit 111 allows the first micro-fluidic channel 104 to be heated to different pre-defined temperature values and to retain these temperature values for pre-defined time intervals. The temperature control unit 111 allows the different temperature values and corresponding time intervals to be changed and set at any moment in time during operation of the device 100. For each temperature value, the related time interval for which the first micro-fluidic channel 104 is heated can be set. According to an embodiment of the disclosure, the temperature values and the related time intervals are set to perform PCR on a fluid sample. According to a specific embodiment of the disclosure, three temperature values and related time intervals at which the first micro-fluidic channel 104 are heated may be set to: 90 to 98 degrees Celsius (e.g. 95 degrees) during 1 to 60 seconds, 60-65 degrees Celsius during 1 to 60 seconds, and 65-75 degrees Celsius during 1 to 60 seconds.

The following example explains the difference between the droplet PCR device described in this disclosure and a state of the art droplet PCR device using cavities.

Example 3

Figure 8:
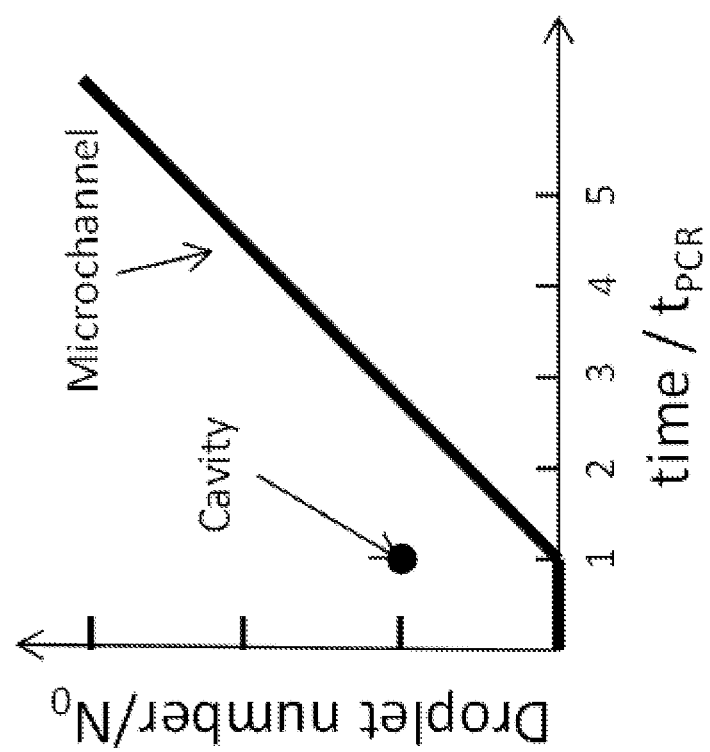
FIG. 8 illustrates a comparison of droplets processed as a function of time using: 1) a state of the art device ("cavity") and 2) an embodiment of the disclosure ("Microchannel")

In this example, a state of the art device comprising a cavity is compared with an embodiment of the disclosure using a micro-fluidic channel. Droplets with diameter d are generated and the length of a side of the cavity of a state of the art device is defined as L. It is assumed that the footprint of each droplet plus the surrounding oil is $2d^2$. In a state of the art device the number of droplets contained in the cavity will be $N_0 = L^2/2d^2$ and the droplets will be processed in a time $t_{PCR}$. In an embodiment of this disclosure, assuming that the micro-fluidic channel has a width d and walls of thickness w, when using the same size as the cavity of the state of the art device, the number of droplets contained in the micro-fluidic channel will be slightly lower: $L^2/2d^2$ $d/(d+w)$. The first 'useful' droplet, e.g. the one that was subjected to a full PCR cycle reaches the outlet of the micro-fluidic channel and is analyzed after a time $t_{PCR}$. From that moment on, the number of analyzed droplets increases at a rate of $L^2/2d^2$ $d/(d+w)/t_{PCR}$. FIG. 8 shows the number of droplets as a function of time for both cases.

According to an embodiment of the disclosure, the temperature control element 111 may be configured to continuously cycle the temperature of the first micro-fluidic channel 104 through at least two temperature values while droplets are being propagated through the first micro-fluidic channel 104. As an advantage, a continuous PCR may be performed on droplets whereby droplets are continuously supplied to the inlet 102 of the first micro-fluidic channel 104 and exiting at the outlet 103 of the first micro-fluidic channel 104. The droplets in the first micro-fluidic channel 104 may be subjected to at least two temperatures (for n times, where n is the number of temperature cycles) before exiting the first micro-fluidic channel 104 via the outlet 103. According to an embodiment of the disclosure, the temperature control unit 111 may be configured to start the cycling of the temperature of the first micro-fluidic channel 104 to at least two temperature values only when droplets are present in the first micro-fluidic channel 104. This configuration allows the device to function as a batch PCR device. In this configuration, after filling the first micro-fluidic channel 104 with the droplets, the droplets in the first micro-fluidic channel 104 are subjected to at least two temperatures. Thereafter, the droplets exit the first micro-fluidic channel 104 via the outlet 103. In this configuration, droplets may be supplied in different batches to the first micro-fluidic channel 104.

It is advantageous that the device 100 as presented in the first aspect of the disclosure may be used as a device for continuous PCR or for batch PCR without changing the design/structure of the device 100. Currently, no state of the art devices exist which are able to perform both functionalities using the same device without physically changing the design.

The first micro-fluidic channel 104 may be an etched channel in a silicon substrate using e.g. CMOS compatible processing techniques. According to another embodiment of the disclosure, the substrate may be a PDMS substrate. The first micro-fluidic channel 104 may be a channel formed in a PDMS substrate using e.g. molding techniques. According to an embodiment of the disclosure, the micro-fluidic device 100 may be completely fabricated in silicon. The fabrication in silicon allows easy monolithic integration of different microfluidic components including filtering, DNA/RNA extraction, reagent mixing, reagents storage etc. As an advantage, it is possible to build a complete digital PCR system in which unprocessed biological samples or bio-fluids can be used. As a further advantage, costs to fabricate may be reduced as the complete device can be fabricated using cheap CMOS compatible processing techniques.

According to an embodiment of the disclosure, the first micro-fluidic channel 104 may feature a meander-like shape. The meander-like shape increases the length of the first micro-fluidic channel 104 and decreases the size and therefore the cost of the complete micro-fluidic device 100. As an advantage, the transit time of droplets (=the time of droplets propagating from the inlet 102 to the outlet 103 of the first micro-fluidic channel 104 may be increased without changing the flow rate (=propagation speed) of droplets in the first micro-fluidic channel 104. As another advantage, compared to state of the art batch PCR devices using cavities, the use of a meander-like shape enables the volume of the first micro-fluidic channel 104 to be comparable to the volume of a cavity. According to an embodiment of the disclosure, the first micro-fluidic channel 104 may feature any other shape which may increase the transit time of droplets in the first micro-fluidic channel 104 for a given flow rate.

According to an embodiment of the disclosure, the droplet generator 107 comprises at least one pump for generating droplets and pumping droplets through the first micro-fluidic channel 104 at a pre-determined flow rate. According to an embodiment of the disclosure, the droplet generator 107 comprises two pumps for controlling a carrier medium (e.g. oil) and a diluent (e.g. water) flow independently. The droplet generator 107 may also comprise a carrier medium (e.g. oil) compartment, an analyte and PCR reagents compartment 113. According to an embodiment of the disclosure, the droplet generator 107 may further comprise a diluent (e.g. water) compartment 112 and a mixer for mixing an analyte and PCR reagents with a diluent.

Figure 2:
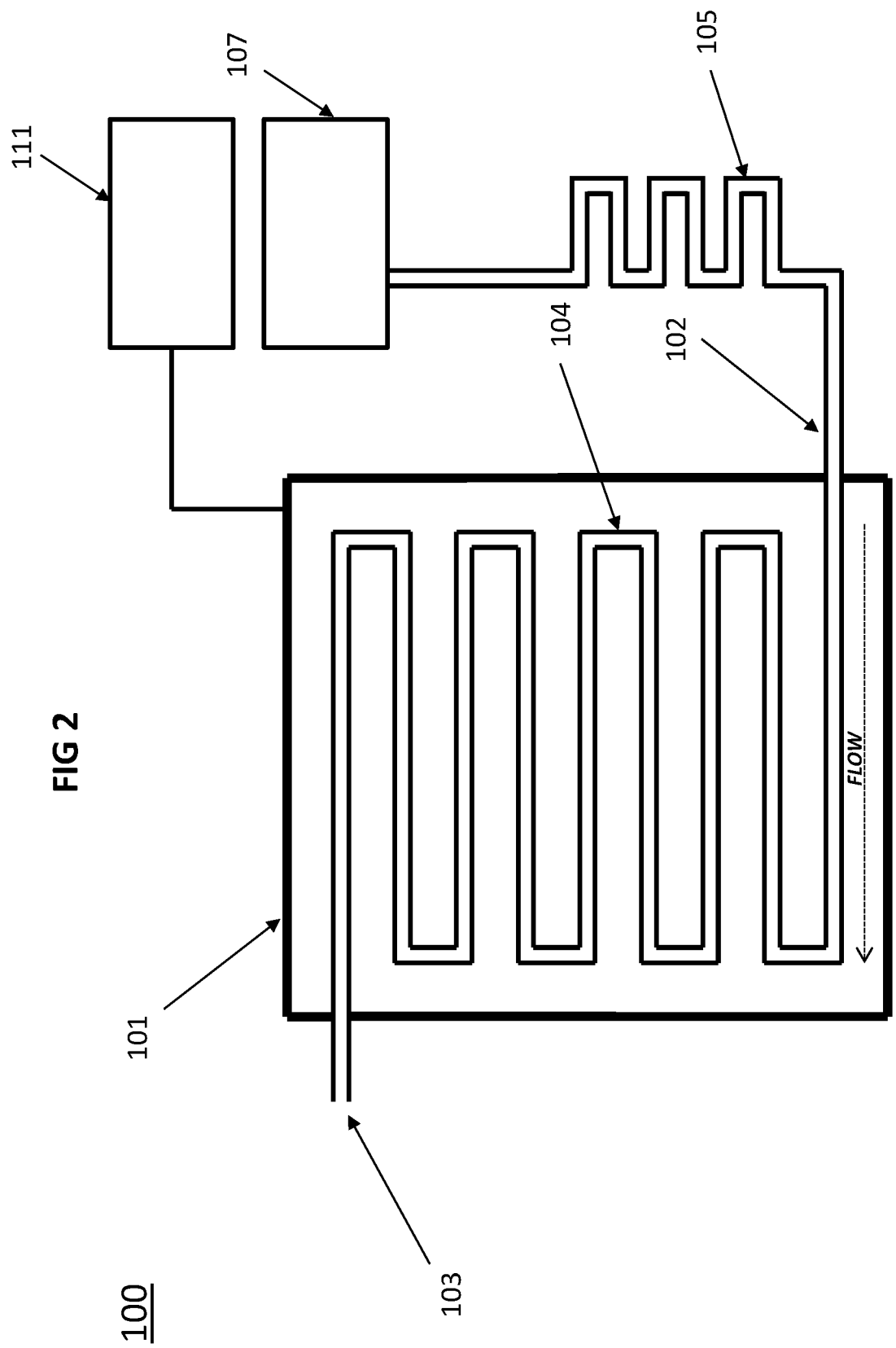
FIG. 2 illustrates an embodiment of the disclosure using a pre-heating element for pre-heating droplets

According to an embodiment of the disclosure, the micro-fluidic device 100 further comprising a second micro-fluidic channel 105 connected on one side to an outlet of the droplet generator 107 and on the other side to the inlet 102 of the first micro-fluidic channel 104; and a heating element located to heat generated droplets present in the second micro-fluidic channel 105. FIG. 2 illustrates such an embodiment.

To heat droplets before they enter the first micro-fluidic channel 104, a heating element is present at the inlet of the first micro-fluidic channel 104. The second micro-fluidic channel 105 interconnects an outlet of the droplet generator 107 to the inlet 102 of the first micro-fluidic channel 104. When performing continuous PCR, the temperature of the first micro-fluidic channel 104 is continuously cycled through at least two temperature values. To avoid droplets entering the first micro-fluidic channel 104 at an unknown temperature, the fluid-sample is pre-heated to a pre-determined temperature. Traditionally, performing a PCR comprises a first step whereby a fluid sample is heated to the DNA denaturation temperature. When starting PCR at a temperature different from the denaturation temperature, non-specific amplification might occur, e.g. DNA fragments different from the chosen ones might be amplified. This may be remedied by pre-heating the droplets before entering the first micro-fluidic channel 104. The generated droplets enter the first microfluidic channel 104 at the temperature of the pre-heating element, e.g. at denaturation temperature. As an advantage, non-specific amplification does not occur. According to an embodiment of the disclosure, the second micro-fluidic channel 105 may feature a meander-like shape.

The meander-like shape functions as a delay element due to the increase in length and allows heating of second micro-fluidic channel 105 in a confined space. As an advantage, area (e.g. silicon) and cost is reduced. Also, the size of the heating element for heating droplets in the second micro-fluidic channel 105 may be reduced.

According to an embodiment of the disclosure, inner dimensions of the first micro-fluidic channel 104 are selected to the size of the generated droplets to only allow single generated droplets to pass through the first micro-fluidic channel 104. According to an embodiment of the disclosure, inner dimensions of the first micro-fluidic channel 104 are selected to allow the surface of each generated droplet to touch all inner surfaces of the first micro-fluidic channel 104 when propagating through the first micro-fluidic channel 104. When performing continuous PCR, the inner dimensions (e.g. width and height or diameter) of the first micro-fluidic channel 104 need to be selected to the size of to be generated droplets. Only single generated droplets, separated by oil, may propagate through the first micro-fluidic channel 104. According to an embodiment of the disclosure, the volume of generated droplets is such that their lateral surface is in contact with the first micro-fluidic channel 104 walls. It is advantageous that only single droplets may pass through the first micro-fluidic channel 104 as this reduces the risk of droplet merging. It is also advantageous to monitor single droplets at the outlet of the first micro-fluidic channel 104.

Figure 3:
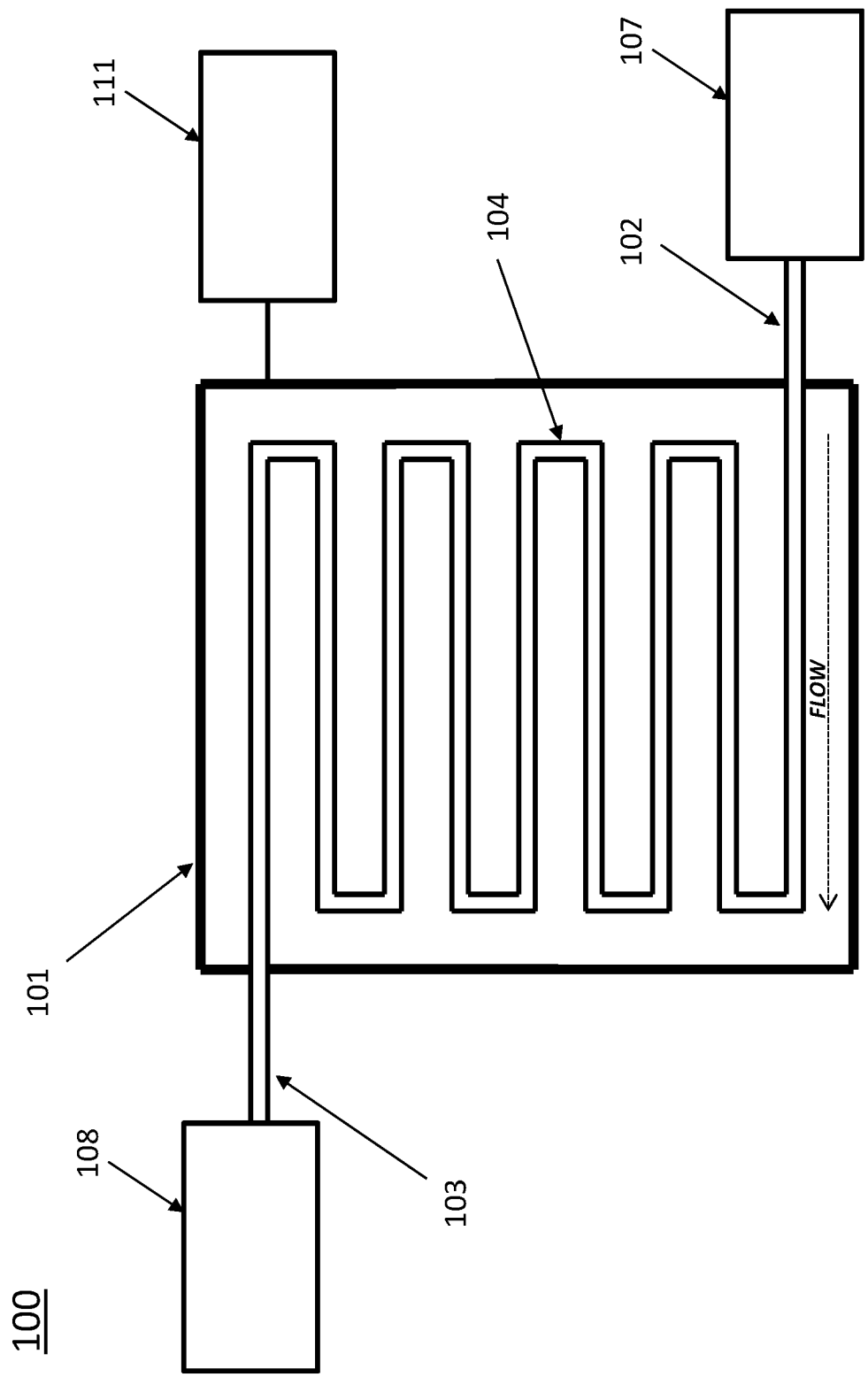
FIG. 3 illustrates an embodiment of the disclosure using a fluorescence detector which is connected to a micro-fluidic channel for detecting droplets

According to an embodiment of the disclosure, the micro-fluidic device 100 further comprises a detector 108 located at the outlet 103 of the first microfluidic channel for detecting droplets containing PCR products. FIG. 3 illustrates such an embodiment.

The presence of an analyte in a droplet can be detected at the outlet 103 of the first micro-fluidic channel 104 using a detector 108 located at the outlet 103 of the first micro-fluidic channel 104. During droplet generation a label may be added to each droplet which emits light on binding with the analyte. Detecting the presence of an analyte in a droplet may be done by detecting the fluorescence of droplets or UV absorbance at the outlet 103 or at the first micro-fluidic channel 104. For detecting UV absorbance, a light source may be used to illuminate droplets at the outlet 103 of the first micro-fluidic channel 104. The detector may be an optical detector such an image sensor. The detector may also be configured to detect multiple droplets at the same time. According to an embodiment of the disclosure, the detector 108 may be part of the device and embedded in the semiconductor substrate. According to another embodiment of the disclosure, the detector 108 may be embedded in a third micro-fluidic channel connected to the outlet 103 of the first micro-fluidic channel 104. The third micro-fluidic channel may be fabricated at least partly from a transparent material to allow emitted light from droplets to travel through the transparent material to a detector 108, being an optical detector, which may be located underneath third micro-fluidic channel. According to an embodiment of the disclosure the optical detector may be a pixel. A spectral filter on top of the optical detector may be used to filter fluorescence from droplets. As an advantage, different analytes may be detected in different droplets.

According to an embodiment of the disclosure, the micro-fluidic device 100 further comprises a detector 108 located for detecting droplets containing PCR products during PCR in the first micro-fluidic channel 104 disclosure.

When the detector 108 is located at the first micro-fluidic channel 104, droplets can be monitored in real-time during PCR. As an advantage, monitoring of droplets during PCR can be used to analyze the amplification speed of an analyte in a droplet. For example, the intensity of the fluorescence or the change of the UV absorption of droplets may be used to derive an amplification curve of an analyte in droplets. The amplification curve may be used to examine amplification behaviour of analytes. As an advantage, as the droplets are monitored during PCR, performing PCR may be halted from the moment PCR is complete. This results in a shorter total time to analysis. The monitoring of the droplets during PCR may be a continuous monitoring wherein a detector 108 is able to monitor individual droplets in the complete first micro-fluidic channel 104. For example, the detector 108 may be an image sensor located underneath the complete first micro-fluidic channel 104 wherein the size of the detector 108 allows monitoring of droplets during propagation through the complete first micro-fluidic channel 104. According to a specific embodiment, a part of the first micro-fluidic channel 104 may be fabricated from a transparent material to allow fluorescence or UV absorbance from droplets to travel through the transparent material to a detector 108.

Figure 4:
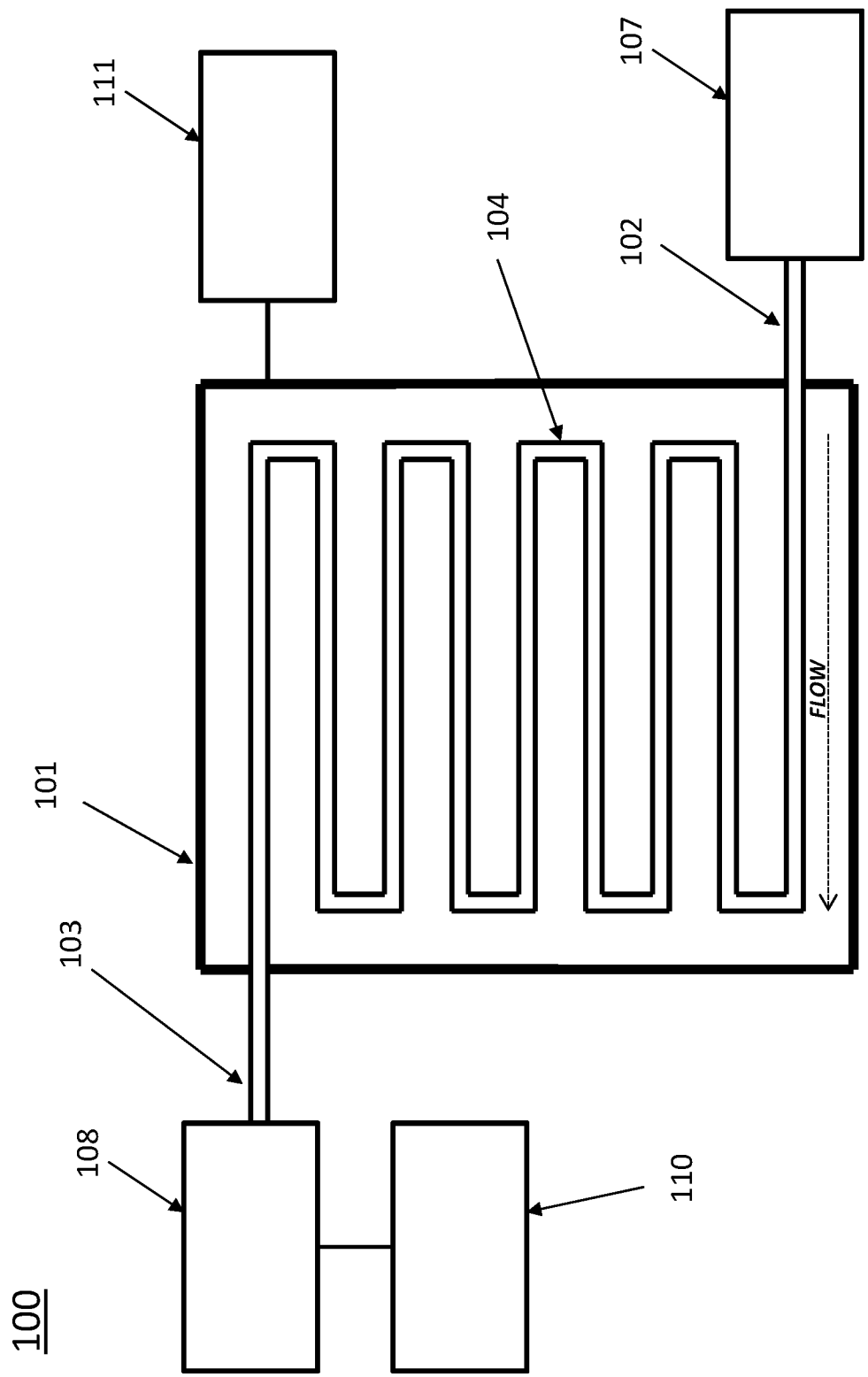
FIG. 4 illustrates an embodiment of the disclosure using a computing unit which is connected to a detector for analyzing data of the detector

According to an embodiment of the disclosure, the micro-fluidic device 100 further comprises a computing unit 110 connected to the detector 108. The computing unit 110 is configured for determining a percentage of droplets containing PCR products. Such an embodiment is illustrated in FIG. 4. The determination of the percentage of droplets containing PCR products may be based on the fluorescence or UV absorbance of droplets.

The computing unit 110 is used to determine the number of droplets containing one or more copies of an analyte. The computing unit 110 may be a processor configured to continuously determine the percentage of droplets containing PCR products based on input data (e.g. an image) of the fluorescence or UV absorbance of droplets from the detector 108.

Figure 5:
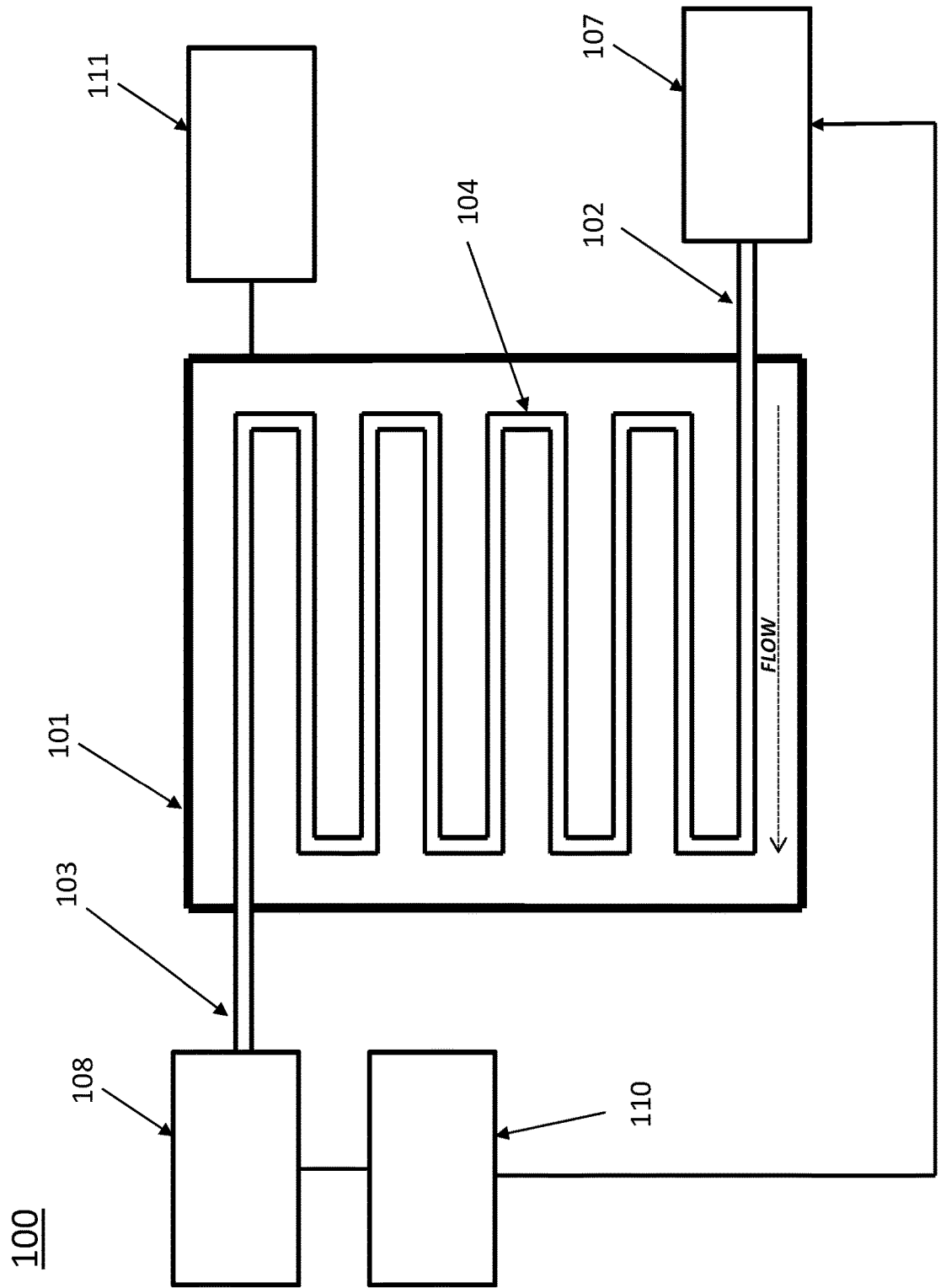
FIG. 5 illustrates an embodiment of the disclosure wherein a computing unit is connected to a droplet generator to change droplet size depending on data from the computing unit

According to an embodiment of the disclosure, the droplet generator 107 is connected to the computing unit 110. The droplet generator 107 may be reconfigured to change the number of copies of an analyte in droplets. Such an embodiment is illustrated in FIG. 5. The reconfiguration may comprise changing the size of droplets. The size of generated droplets may be changed to change the average number of copies of an analyte in a droplet depending on the percentage of fluorescent droplets. For example, if the percentage of fluorescent droplets is too high, the volume of the droplets can be reduced. This can be achieved by increasing the oil flow and decreasing the analyte flow. At any moment in time, the number of copies of an analyte in droplets can be changed by the droplet generator 107 depending on the percentage of fluorescent droplets determined by the computing unit 110.

The computing unit 110 may continuously analyze generated droplets. The analysis may comprise determining the percentage of fluorescent droplets. The information on the percentage of fluorescent droplets may be coupled back to the reconfigurable droplet generator 107 to adjust the number of copies of an analyte in generated droplets. The continuous analysis of droplets allows, by means of a feedback loop, to bring the system closer to an optimum accuracy. The following example explains this.

Example 4

After analyzing a relatively small number of droplets it can be noticed that all or a large part of the droplets are fluorescent. This may indicate that the number of copies of the analyte per droplet is too high. In this case the droplet generator 107 may be used to generate smaller droplets which contain a lower number of copies of the analyte per droplet. When the size of droplets cannot be reduced further, an appropriate dilution system may be used.

According to an embodiment of the disclosure, the droplet generator 107 comprises a configurable dilution system. The dilution value of the dilution system can be set optimally based on a limited number of droplets which are analyzed by the detector 108 and the computing unit 110. It is an advantage that neither interruption of the experiment nor the loading of a new fluid sample is required to perform the tweaking of the number of copies of an analyte in generated droplets.

According to an embodiment of the disclosure, the droplets may comprise an analyte and PCR reagents mixed together with a diluent. For example, the reagents may be a polymerase or a polymerase variant, salts, buffers for pH adjustments, nucleotides among others. For example, the diluent may be water. The ratio in which the different components are mixed together defines the concentration of the analyte in droplets. The analyte may be e.g. DNA from different origin. The droplet generator may generate droplets and separate the droplets from each other by using oil. The oil may be a mineral or a fluorinated oil.

According to an embodiment of the disclosure, the amount of analyte and PCR reagents and the amount of diluent can be changed to change the number of copies of the analyte in generated droplets based on analyzed droplets at the outlet 103 of the first micro-fluidic channel 104.

According to an embodiment of the disclosure, the droplet generator 107 is configured to add at least one label to each generated droplet which emits light on binding with the analyte, e.g. when binding to DNA.

According to an embodiment of the disclosure, the micro-fluidic device 100 further comprises a thermo-cooling element for cooling the complete first micro-fluidic channel 104. According to an embodiment of the disclosure, the thermo-cooling element may be connected to the thermal control unit. The thermo-cooling element may also act as a heating element.

The thermo-cooling element may be positioned near or underneath the first micro-fluidic channel 104 and may be used to cool the first micro-fluidic channel 104 during cycling of the temperature (during PCR). As an advantage, the thermo-cooling element may reduce the total time needed to cycle the first micro-fluidic channel 104 through different temperature values.

Figure 6:
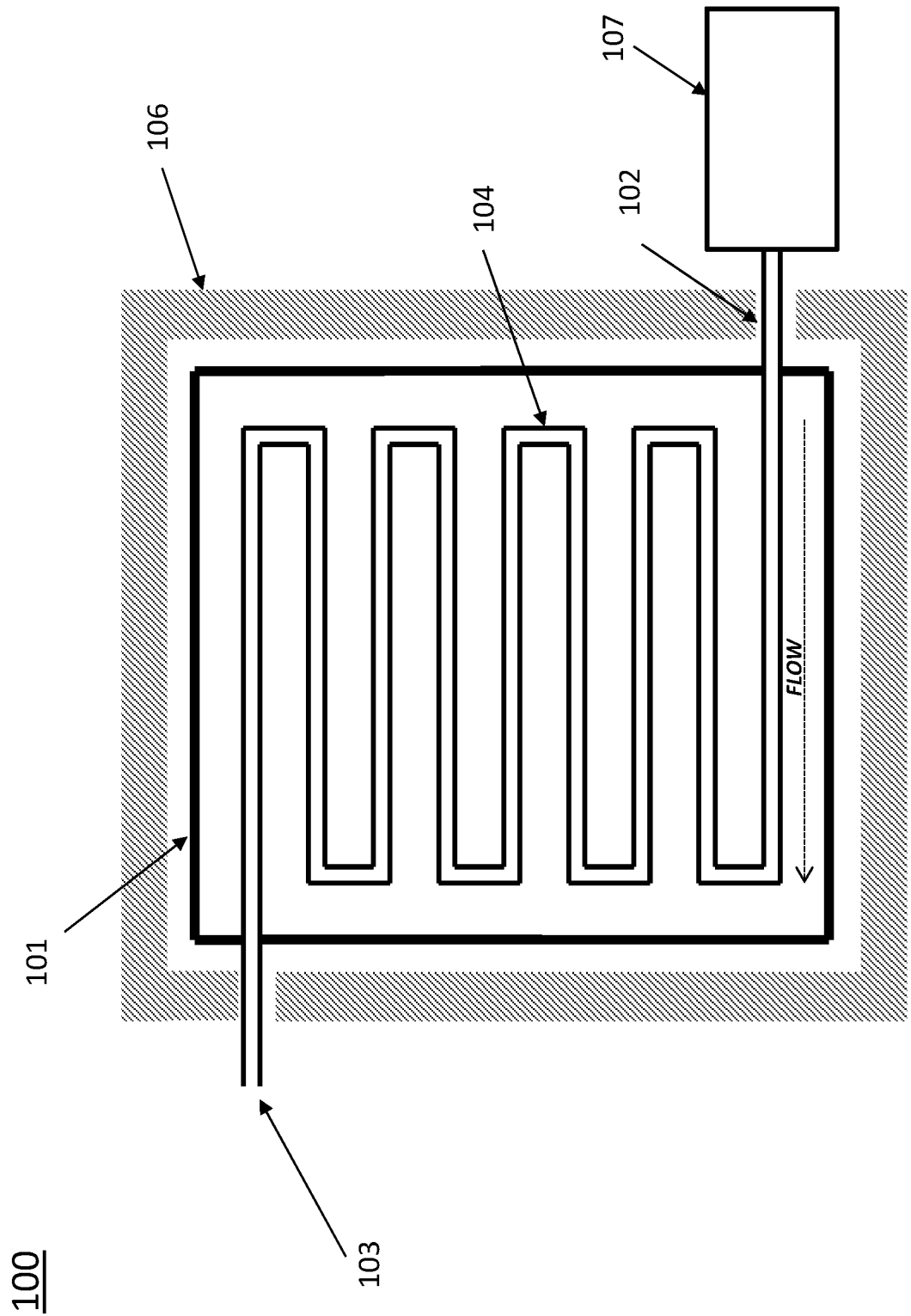
FIG. 6 illustrates an embodiment of the disclosure wherein a through-substrate trench at least partially surrounds the micro-fluidic channel
Figure 7:
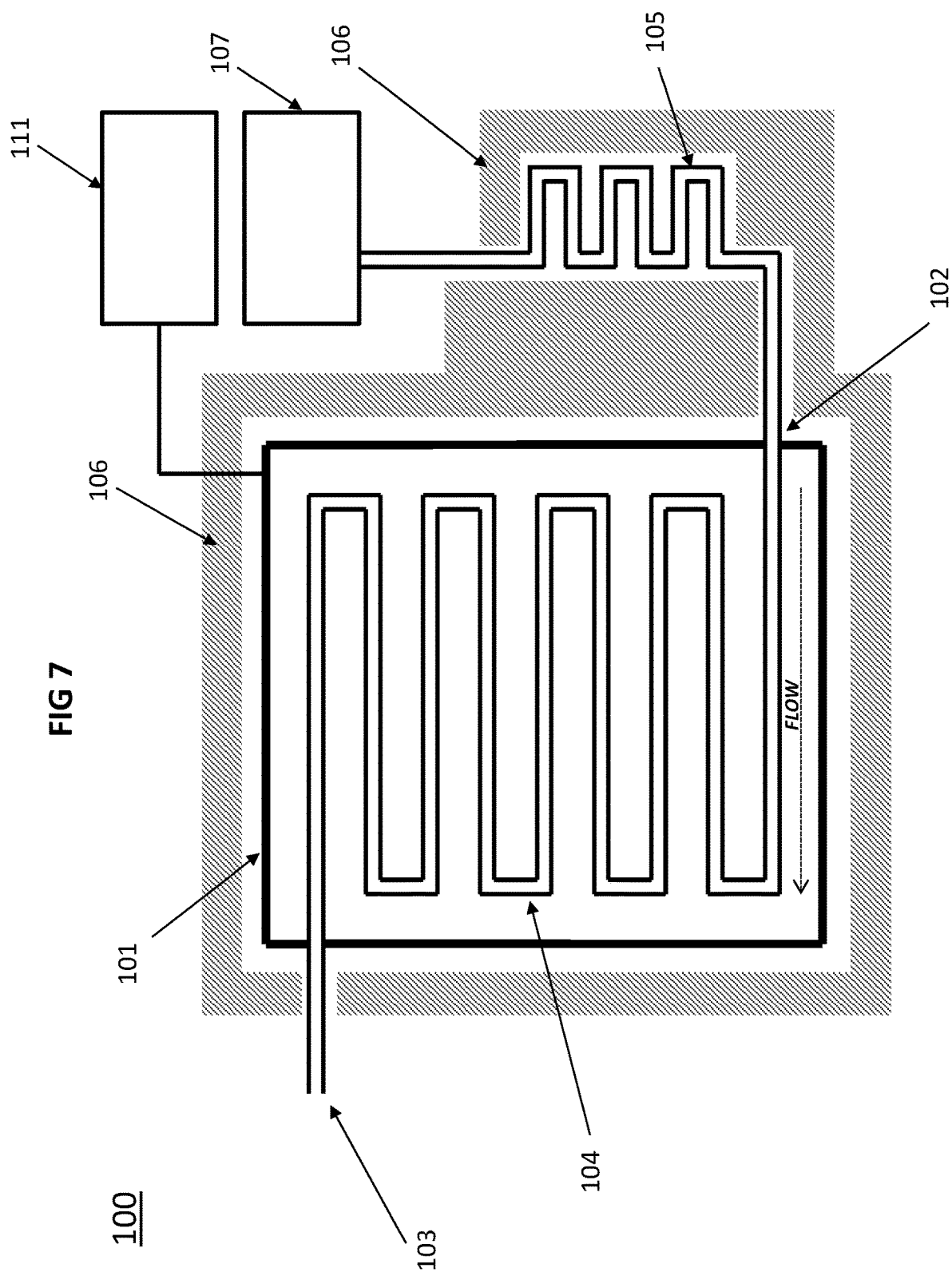
FIG. 7 illustrates an embodiment of the disclosure wherein a through-substrate trench partially surrounds the micro-fluidic channel and a pre-heating element for pre-heating droplets

According to an embodiment of the disclosure, the micro-fluidic device 100 further comprises at least one through-substrate trench 106 at least partially surrounding the first micro-fluidic channel 104. Such an embodiment is illustrated in FIG. 6. According to an embodiment of the disclosure, the second micro-fluidic channel 105 is at least partially surrounded by a through-substrate trench. Such an embodiment is illustrated in FIG. 7.

The first micro-fluidic channel 104 may be separated from the rest of the substrate by partially or fully surrounding the first micro-fluidic channel 104 with a through-substrate trench 106. The trench insulates the first micro-fluidic channel 104 from the rest of the substrate and reduces the physical and thermal mass of the reactor. Heating a small mass which is thermally insulated results in a short thermal time constant. Thus, the first micro-fluidic channel 104 can be heated to a certain temperature in a shorter period of time. The through-substrate trench also makes sure that other components on or in the substrate are not heated up. In this case, the trench functions as a thermal barrier to reduce the temperature of different components on the micro-fluidic device.

According to an embodiment of the disclosure, the semiconductor substrate of the micro-fluidic device 100 may be bonded, e.g. anodically bonded, to a cover layer, e.g. a Pyrex cover layer, for sealing micro-fluidic components of the micro-fluidic device. The cover layer also acts as a support for the micro-fluidic components which are surrounded by a through-substrate trench.

According to an embodiment of the disclosure, the device described in the first aspect of the disclosure and its embodiments may be a lab-on-a-chip. All components of the micro-fluidic device may be fabricated in silicon using CMOS compatible processing techniques. This allows the device to be manufactured in a miniaturized and cost effective way. According to a specific embodiment, the device may have dimensions of 3 mm by 3 mm or 10 mm by 10 mm or 20 mm by 20 mm.

According to an embodiment of the disclosure, the micro-fluidic device 100 may comprise a transistor layer for electrically connecting and controlling electrical components on the device, e.g. MEMS components, pumps, heaters. The transistor layer may be embedded in the semiconductor substrate of the micro-fluidic device 100.

According to an embodiment of the disclosure, an inlet of a droplet generator 107 may be connected to a micro-fluidic block configured for preparing a fluid sample. The micro-fluidic block may be part of the micro-fluidic device. The micro-fluidic block prepares a fluid sample before generating droplets from the fluid sample. The preparation steps may comprise purification or extraction steps to purify a fluid sample or extract an analyte from a fluid sample. As an advantage, the micro-fluidic block allows the micro-fluidic device 100 to be used for a wide range of fluid samples such as biological samples or bio-fluids whereby no additional manual preparation steps need to be performed prior to providing it to the micro-fluidic device 100.

According to an embodiment of the disclosure, a heating element is located at the outlet 103 of the first micro-fluidic channel 104. The heating element may be configured to continuously heat droplets to increasing temperatures. The temperature of the heating element can be increased for a certain period of time, e.g. increasing the temperature of the heating element for 10 minutes. The droplets are exposed to continuously increasing temperatures, e.g. an increasing temperature from 60 to 90 degrees Celsius within 10 minutes. By continuously increasing the temperature to heat the droplets at the outlet, a melting curve analysis of PCR products can be performed. As an advantage, the melting curve analysis can be used as a control for specificity.

In a second aspect of the disclosure, a method to perform PCR using a device as described in the first aspect of the disclosure is presented. The method comprises: providing a fluid sample in the micro-fluidic device 100 according to the first aspect of the disclosure and any of its embodiments; generating droplets of the fluid sample and pumping the droplets into the first micro-fluidic channel 104 using the droplet generator 107; cycling the temperature of the complete first micro-fluidic channel 104 through at least two temperature values using the temperature control unit 111.

According to an embodiment of the disclosure, providing a fluid sample in the micro-fluidic device 100 comprises providing a diluent, a sample and PCR reagents and a carrier medium (e.g. oil) to the droplet generator 107. The droplet generator 107 generates droplets of a pre-determined size and supplies the droplets and the carrier medium (e.g. oil) using a pump at an adaptable flow rate to the first micro-fluidic channel 104 of the micro-fluidic device 100. The temperature control unit 111 is used to control the heating element 101 and for heating the first micro-fluidic channel 104 to at least two temperature values to perform PCR on the droplets.

According to an embodiment of the disclosure, generating droplets and pumping droplets is stopped when the first micro-fluidic channel 104 is completely filled with droplets.

When performing batch PCR, in a first stage the first micro-fluidic channel 104 is partly or completely filled with droplets. In a second stage, a PCR is performed on the droplets. The droplet generator 107 generates droplets and pumps the droplets into the first micro-fluidic channel 104 until the first micro-fluidic channel 104 is partly or completely filled with droplets. Thereafter, the pumping is stopped. Thereafter, the temperature of the first micro-fluidic channel 104 is cycled to at least two temperature values to perform a PCR cycle on the droplets. Thereafter, the droplets may be pumped out of the first micro-fluidic channel 104 and newly generated droplets may be provided in the first micro-fluidic channel 104 for performing a new PCR operation. This procedure may be repeated.

According to an embodiment of the disclosure, cycling the temperature of the first micro-fluidic channel 104 is performed until a saturation level of an analyte in a droplet is reached.

The cycling of the temperature is stopped when the saturation stage of the PCR has been reached. At this stage, the PCR cycle is complete and the droplets in the first micro-fluidic channel 104 can be pumped out of the first micro-fluidic channel 104. This operation can be repeated whereby a new batch of droplets is supplied into the first micro-fluidic channel 104 until partly or completely filled and thereafter PCR is performed again.

According to an embodiment of the disclosure, cycling the temperature of the first micro-fluidic channel 104 comprises continuously cycling the temperature of the first micro-fluidic channel 104 through at least two temperature values whilst pumping droplets into the first micro-fluidic channel 104.

To perform continuous PCR, droplets are generated by the droplet generator 107 and are pumped into the first micro-fluidic channel 104. The droplets in the first micro-fluidic channel 104 are always in motion. As the droplets travel from the inlet 102 of the first micro-fluidic channel 104 to the outlet 103 of the first micro-fluidic channel 104, the temperature of the first micro-fluidic channel 104 is continuously cycled through at least two temperature values.

According to an embodiment of the disclosure, the droplets are pumped in the first micro-fluidic channel 104 at a flow rate adapted to a duration of the temperature cycling of the first micro-fluidic channel 104.

The propagation speed of droplets in the first micro-fluidic channel 104 is defined by the flow rate of the droplet generator 107. This flow rate is adapted to a duration of the temperature cycling of the first micro-fluidic channel 104. As an advantage, the flow rate of the droplets in the first micro-fluidic channel 104 and a temperature cycling of the first micro-fluidic channel 104 can be adapted to each other. The flow rate of droplets in the first micro-fluidic channel 104 can be adjusted to the number of desired temperature cycles wherein each temperature cycle comprises at least two temperature values.

According to an embodiment of the disclosure, the method further comprises pre-heating the generated droplets before pumping the droplets into the first micro-fluidic channel 104. This pre-heating may be done using a heating element.

According to an embodiment of the disclosure, the generated droplets are heated to a pre-defined temperature (e.g. the denaturation temperature of an analyte to be amplified) before entering the first micro-fluidic channel 104. The generated droplets enter the first microfluidic channel 104 at a pre-determined temperature. When performing continuous PCR, the temperature of the first micro-fluidic channel 104 is continuously cycled through at least two temperature values. To avoid droplets entering the first micro-fluidic channel 104 at an unknown temperature, the droplets are pre-heated to a pre-determined temperature. Traditionally, performing a PCR comprises a first step whereby a fluid sample is heated to a denaturation temperature. Starting the process at a temperature different from the denaturation temperature might cause non-specific amplification, e.g. DNA fragments different from the chosen one might be amplified. This is solved by pre-heating the droplets. For example, the generated droplets enter the first microfluidic channel 104 at the temperature of the pre-heating element, e.g. at a denaturation temperature of the analyte.

According to an embodiment of the disclosure, the method further comprises detecting droplets at the outlet 102 using the detector 108. According to an embodiment of the disclosure, the detection of droplets containing PCR products comprises detecting fluorescence of droplets or determining UV absorption of droplets using the detector.

When performing continuous PCR, droplets are continuously pumped into the first micro-fluidic channel 104. Droplets can be monitored continuously at the outlet 103 of the first micro-fluidic channel 104. Information from monitored droplets, e.g. fluorescence or UB absorption, may be used as feedback to the droplet generator 107 to change the number of copies of an analyte in droplets if necessary. According to an embodiment of the disclosure, the number of copies of an analyte in droplets is changed by the droplet generator 107 depending on the percentage of droplets containing PCR products determined by the computing unit 110. The number of copies of an analyte in droplets may be changed using a dilution system which may be part of the droplet generator 107. Alternatively, the number of copies of an analyte in droplets may be changed by changing the size of droplets by the droplet generator 107. As an advantage, the feedback system may be used to fine-tune the micro-fluidic device 100 in real-time. Such a fine-tuning during operation is not possible in state of the art devices.

According to an embodiment of the disclosure, the method further comprises counting droplets comprising PCR products using the detector 108. According to an embodiment of the disclosure, after detecting droplets, the droplets may be sorted based on the fluorescence or UV absorbance of the droplets.

The invention claimed is:

1. A method for performing continuous PCR on a fluid sample using a micro-fluidic device, the fluid sample comprising an analyte, the method comprising:
    continuously providing the fluid sample in the micro-fluidic device, the micro-fluidic device comprising
        a semiconductor substrate;
        a first micro-fluidic channel, comprising an inlet and an outlet, embedded in the semiconductor substrate;
        a single heating element configured for cycling a temperature of the first micro-fluidic channel through at least two temperature values, the heating element thermally coupled to the first micro-fluidic channel;
        a droplet generator connected to the inlet of the first micro-fluidic channel and configured for generating droplets of the fluid sample and pumping the generated droplets into the first micro-fluidic channel, the droplet generator is reconfigurable for changing a number of copies of the analyte in the droplets;
        a detector located at the outlet of the first micro-fluidic channel and configured for detecting droplets containing PCR products following PCR in the first micro-fluidic channel, the PCR products comprising the copies of the analyte; and
        a computing unit connected to the detector and to the droplet generator and configured for continuously monitoring and determining a percentage of droplets containing PCR products based on input data from the detector and for reconfiguring the droplet generator to change the number of the copies of the analyte in the droplets to a pre-determined level based on the percentage of droplets;
    continuously generating droplets of the fluid sample and pumping the droplets into the first micro-fluidic channel using the droplet generator;
    continuously cycling the temperature of the first micro-fluidic channel through the at least two temperature values using the heating element while continuously pumping the droplets into the first micro-fluidic channel;
    continuously detecting droplets containing the PCR products using the detector; and
    continuously monitoring and determining the number of droplets containing the copies of the analyte and reconfiguring the droplet generator to change the number of copies of the analyte in the droplets using the computing unit to continuously adjust a carrier flow rate and an analyte flow rate and optionally a diluent flow rate of the droplet generator, depending on the percentage of droplets containing PCR products as determined by the computing unit.

2. The method according to claim 1, wherein said generating droplets and pumping the droplets is stopped when the first micro-fluidic channel is completely filled with the droplets.

3. The method according to claim 1, wherein the droplets are pumped at a flow rate adapted to a duration of the temperature cycling of the first micro-fluidic channel.

4. The method according to claim 1, further comprising: pre-heating the generated droplets before pumping the droplets into the first micro-fluidic channel.

5. The method according to claim 1, wherein the micro-fluidic device further comprises a heating element present at the inlet of the first micro-fluidic channel and a second micro-fluidic channel, the second micro-fluidic channel connected on one side to an outlet of the droplet generator and on the other side to the heating element present at the inlet of the first micro-fluidic channel, wherein the heating element located at the inlet of the first micro-fluidic channel pre-heats the droplets prior to being pumped into the first micro-fluidic channel.

6. The method according to claim 1, wherein the micro-fluidic device further comprises at least one through-substrate trench at least partially surrounding the first micro-fluidic channel.

* * * * *